United States Patent
Schwach et al.

(10) Patent No.: US 10,765,721 B2
(45) Date of Patent: *Sep. 8, 2020

(54) MANUFACTURE OF DEGARELIX

(71) Applicant: Ferring B.V., Hoofddorp (NL)

(72) Inventors: Grégoire Schwach, Copenhagen (DK); Anders Nilsson, Lund (SE); Tine Elisabeth Gottschalk Bøving, Lyngby (DK); Jon Holbech Rasmussen, Lyngby (DK); Birgitta Mörnstam, Limhamn (SE); Anders Tsirk, Malmö (SE); Ulf Annby, Lund (SE); Jens Fomsgaard, Farum (DK)

(73) Assignee: Ferring B.V, Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/224,843

(22) Filed: Dec. 19, 2018

(65) Prior Publication Data

US 2019/0224271 A1    Jul. 25, 2019

Related U.S. Application Data

(63) Continuation of application No. 15/420,156, filed on Jan. 31, 2017, now Pat. No. 10,172,906, which is a continuation of application No. 14/403,775, filed as application No. PCT/EP2013/061264 on May 31, 2013, now Pat. No. 9,592,266.

(30) Foreign Application Priority Data

Jun. 1, 2012    (EP) .................................... 12170454

(51) Int. Cl.
| | | |
|---|---|---|
| *A61K 9/19* | (2006.01) | |
| *A61K 38/09* | (2006.01) | |
| *C07K 7/06* | (2006.01) | |
| *A61K 38/08* | (2019.01) | |
| *A61K 38/25* | (2006.01) | |
| *A61K 9/00* | (2006.01) | |
| *A61K 47/26* | (2006.01) | |
| *A61K 9/16* | (2006.01) | |
| *A61K 47/12* | (2006.01) | |

(52) U.S. Cl.
CPC ............ *A61K 38/08* (2013.01); *A61K 9/0019* (2013.01); *A61K 9/0024* (2013.01); *A61K 9/1623* (2013.01); *A61K 9/19* (2013.01); *A61K 38/09* (2013.01); *A61K 38/25* (2013.01); *A61K 47/12* (2013.01); *A61K 47/26* (2013.01); *C07K 7/06* (2013.01)

(58) Field of Classification Search
CPC ...... A61K 9/0024; A61K 9/1623; A61K 9/19; A61K 38/08; A61K 38/09; A61K 47/12; A61K 47/26; C07K 7/06
See application file for complete search history.

(56) References Cited

U.S. PATENT DOCUMENTS

| | | |
|---|---|---|
| 3,773,919 A | 11/1973 | Boswell |
| 5,506,207 A | 4/1996 | Rivier et al. |
| 5,516,887 A | 5/1996 | Deghenghi |
| 5,595,760 A | 1/1997 | Cherif-Cheikh |
| 5,821,230 A | 10/1998 | Jiang et al. |
| 5,860,957 A | 1/1999 | Jacobsen et al. |
| 5,863,549 A | 1/1999 | Taratino |
| 5,925,730 A | 7/1999 | Semple et al. |
| 6,214,798 B1 | 4/2001 | Semple et al. |
| 6,503,534 B1 | 1/2003 | Pellet et al. |
| 6,875,843 B2 | 4/2005 | Jacobson |
| 9,415,085 B2 | 8/2016 | Van Der Meulen et al. |
| 9,579,359 B2 | 2/2017 | Olesen et al. |
| 9,592,266 B2 | 3/2017 | Schwach et al. |
| 10,172,906 B2 * | 1/2019 | Schwach ................ A61K 38/25 |
| 2004/0038903 A1 | 2/2004 | Luck et al. |
| 2004/0138610 A1 | 7/2004 | Cormier et al. |
| 2005/0245455 A1 | 11/2005 | Luck et al. |
| 2005/0276854 A1 * | 12/2005 | Trigg ................... A61K 9/0024 424/473 |
| 2005/0282731 A1 | 12/2005 | Bauer et al. |
| 2006/0135405 A1 | 6/2006 | Rischer et al. |
| 2008/0032935 A1 | 2/2008 | Engel et al. |
| 2009/0018085 A1 | 1/2009 | Luck et al. |
| 2009/0203622 A1 | 8/2009 | Persson |
| 2009/0209939 A1 | 8/2009 | Verespej et al. |

(Continued)

FOREIGN PATENT DOCUMENTS

| | | |
|---|---|---|
| CN | 1411803 A | 4/2003 |
| CN | 102204889 | 5/2012 |

(Continued)

OTHER PUBLICATIONS

"Alkaline Phosphatase," GP Notebook (Sep. 12, 2011), http://gpnotebook.co.uk/simplepage.cfm?ID=-1932525548.
Agerso, et al., "The dosing solution influence on the pharmacokinetic of degarelix, a new GnRH antagonist, after s.c. administration to beagle dogs," European Journal of Pharmaceutical Sciences, vol. 20, pp. 335-340, 2003.
Albertsen et al., Reduced Risk of Cardiovascular (CV) Events and Death in Patients (PTS) Receiving Degarelix Compared with LHRH Agonists (2012).
Albertsen, et al. "Cardiovascular Morbidity Associated with Gonadotropin Releasing Hormone Agonist and an Antagonist," European Urology (2013), https://dx.doi.org/10.16/j.eururo.2013.10,032.
Andersson et al., "Large-Scale Synthesis of Peptides," Biopolymers (Peptide Science), pp. 227-250, 2000.

(Continued)

*Primary Examiner* — Jeffrey E. Russel
(74) *Attorney, Agent, or Firm* — Finnegan, Henderson, Farabow, Garrett & Dunner, LLP

(57) ABSTRACT

The present invention provides methods for producing a lyophilized degarelix product which, upon reconstitution with water for injection in an amount of 20 mg/ml, shows a viscosity of up to 15 mPas. The present invention also provides a lyophilized degarelix drug substance which shows, upon dissolution in water in an amount of 20 mg/ml, a viscosity of up to 3.2 mPas, and processes for providing this lyophilized degarelix drug substance.

19 Claims, 3 Drawing Sheets

(56) References Cited

U.S. PATENT DOCUMENTS

Figure 1:
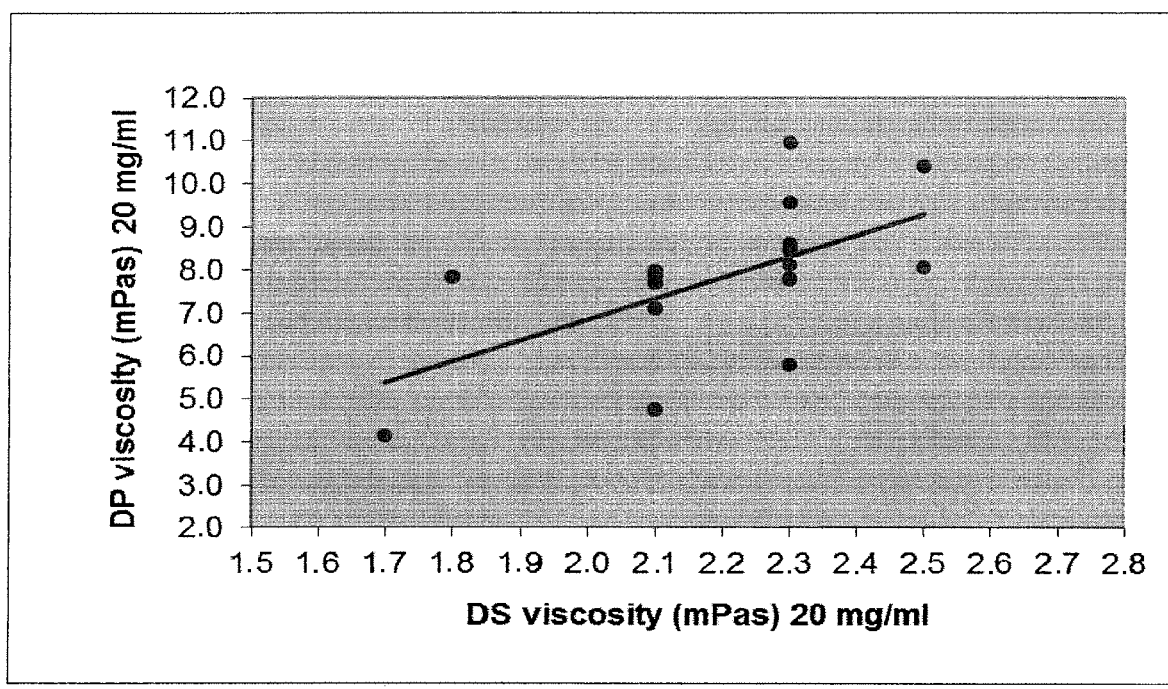

| | | |
|---|---|---|
| 2010/0286603 A1 | 11/2010 | Winderstrom |
| 2010/0305042 A1 | 12/2010 | Olesen et al. |
| 2011/0039787 A1 | 2/2011 | Petri et al. |
| 2011/0053846 A1 | 3/2011 | Luck et al. |
| 2012/0172302 A1 | 7/2012 | Petri et al. |
| 2013/0018223 A1 | 1/2013 | Joseph |
| 2013/0029910 A1 | 1/2013 | Meulen et al. |
| 2013/0281661 A1 | 10/2013 | Rasmusse et al. |
| 2013/0281662 A1 | 10/2013 | Kalita et al. |
| 2013/0295166 A1 | 11/2013 | Grenier et al. |

FOREIGN PATENT DOCUMENTS

| | | |
|---|---|---|
| EP | 0 002 749 B1 | 10/1983 |
| EP | 0 556 034 A1 | 8/1993 |
| EP | 1 003 774 B1 | 5/2000 |
| EP | 1630169 | 8/2007 |
| EP | 1 967 202 A1 | 9/2008 |
| FR | 2 776 520 A | 10/1999 |
| WO | WO 97/34923 | 9/1997 |
| WO | WO 98/46634 | 10/1998 |
| WO | WO 99/26964 A1 | 6/1999 |
| WO | WO 2003/006049 A1 | 10/2003 |
| WO | WO 2006/069779 A2 | 7/2006 |
| WO | WO 2007/130809 A2 | 11/2007 |
| WO | WO 2008/135989 A1 | 11/2008 |
| WO | WO 2009/090189 A1 | 7/2009 |
| WO | WO 2009/101533 A1 | 8/2009 |
| WO | WO 2010/121835 | 4/2010 |
| WO | WO 2011/004260 A2 | 1/2011 |
| WO | WO 2011/066386 A1 | 6/2011 |
| WO | WO 2012/013331 A2 | 2/2012 |
| WO | WO 2012/055905 | 5/2012 |

OTHER PUBLICATIONS

Austria_Codex Fachinformation 2006/2007.
Bak et al., "Physicochemical and Formulation Developability Assessment for Therapeutic Peptide Delivery—A Primer," the AAPS Journal, vol. 17, No. 1, pp. 144-155, Jan. 2015.
Behn, et al., "The obesity epidemic and its cardiovascular consequences," (2006) Curr. Opin. Cardiol. vol. 21, pp. 353-360.
Berges, et al., "Effect of a new leuprorelin formulation on testosterone levels in patients with advanced prostate cancer," (2006), Cur. Med. Res. Opin., vol. 22, No. 4, pp. 649-655.
Boccon-Gibod et al: "Optimising Hormone Therapy in Advanced Disease" European Urology Supllements, vol. 4, No. 8, Nov. 1, 2005 (Nov. 1, 2005), pp. 21-29, XP005112815 ISSN: 1569-9056.
Boccon-Gibod, et al., "Cyproterone Acetate Lead-In Prevents Initial Rise of Serum Testosterone Induced by Luteinizing Hormone-Releasing Hormone Analogs in the Treatment of Mestastatic Carcinoma of the Prostate," (1986) Euro. Urol.,vol. 12, pp. 400-402.
'Bone Specific Alkaline Phosphatase,' The University of Iowa (UIHC), Department of Pathology, Laboratory Services Handbook (Sep. 11, 2011), http://www.healthcare.uiowa.edu/path_handbook/handbook/test2238.html.
Boyle et al: "Treatment of hormone sensitive prostate cancer" European Journal of Cancer. Supplement, Pergamon, Oxford, GB, vol. 3, No. 3, Oct. 1, 2005 (Oct. 1, 2005), pp. 331-338, XP005130027 ISSN: 1359-6349.
Bray, "Large-Scale manufacture of peptide therapeutics by chemical synthesis," Nature Review, vol. 2, pp. 587-593, Jul. 2003.
Broqua et al., "Effects of the New GNRH Antagonist FE200486 one the Growth of the Adrogen-Dependent Prostate Tumor Dunning R-3327H, 6th International Symposium on GnRH Analogues in Cancer and Human Reproduction," Geneva, Switzerland,Feb. 8, 2001.
Broqua, et al., "Pharmacological Profile of a New, Potent, and Long-Acting Gonadotropin-Releasing Hormone Antagonist: Degarelix," The Journal of Pharmacology and Experimental Therapeutics, vol. 301, pp. 95-102, 2002.

Cancer Trends Progress Report, 2001; 2003 Update; 2005 Update; 2007 Update; 2009/2010 Update, http://progressreport.cancer.gov. (last visited Jun. 1, 2012).
Cetrotide TM package insert (Aug. 11, 2000).
Chernecky, and Berger, "Laboratory Tests and Diagnostic Procedures," (2008) Fifth Edition, WB Saunders & Company, Philadelphia. ISBN-978-1-14160-3704-0.
Council of Europe, Strasbourg, "European Pharmacopoeia 6263" European Directorate for the Quality of Meicines & Healthcare (2007).
Council of Europe, Strasbourg, "European Pharmacopoeia6748" European Directorate for the Quality of Meicines & Healthcare (2007).
Crawford et al., "A Phase III Extension Trial With a 1-Arm Crossover From Leuprolide to Degarelix: Comparison of Gonadotropin-Releasing Hormone Agonist and Antagonist Effect of Prostate Cancer," 186 The Journal of Urology 889-897 (2011).
Crawford et al., "Long term tolerability and efficacy of degarelix: 5-year results from a phase III extension trial with a one-arm crossover from leuprolide to degarelix", Urologic Oncology, School of Medicine, University of Colorado Denver, pp. 1-18; Mar. 22, 2014.
Crawford et al., Degarelix Versus LHRH Agonists: Differential Skeletall Morbidity Outcomes from a Pooled Analysis of Six Comparative Randomised Clinical Trials (2012).
De la Rosette et al., "Efficacy and safety of androgen deprivation therapy after switching from monthly leuprolide to monthly degarelix in patients with prostate cancer," 65(5) International Journal of Clinical Practice 559-66 (2011).
De Pinieux, et al., "Clinical and Experimental Progression of a New Model of Human Prostate Cancer and Therapeutic Approach," American Journal of Pathology, vol. 159, No. 2, Aug. 2001, 753-764.
Debruyne Franse M J: "Gonadotropin-releasing hormone antagonist in the management of prostate cancer." Reviews in Urology 2004, vol. 6 Suppl 7, 2004, pp. S25-S32, XP002527257 ISSN: 1523-6161.
Debruyne, et al., "Abarelix for injectable suspension: first-in-class gonadotropin-releasing hormone antagonist for prostate cancer," (2006) Future Oncol., vol. 2, pp. 677-696.
Degarelix Study Group Tammela et al: "904Degarelix—a phase 11 multicenter, randomized dose-escalating study testing a novel gnrh receptor blocker in prostate cancer patients" Euorpean Urology Supplements, vol. 4, No. 3, Mar. 1, 2005 (Mar. 1, 2005), p. 228, XP005007365 ISSN: 1569-9056.
Demers et al., "Biochemical Markers and Skeletal Metastases," Cancer, vol. 88, pp. 2919-2926, Mar. 2, 2000.
Denis, et al., "Overview of Phase III Trials on Combined Androgen Treatment in Patients with Metastatic Prostate Cancer," (1993) Cancer, vol. 72, pp. 3888-3895.
Doehn Christian et al: "Drug evaluation: Degarelix—a potential new therapy for prostate cancer." Idrugs: The Investigational Drugs Jounral Aug. 2006, vol. 9, No. 8, Aug. 2006 (Aug. 2006), pp. 565-572, XP009105353 ISSN: 1369-7056.
Eastman et al., "Serum Alkaline Phosphatase: Normal Values by Sex and Age," 23(9) Clinical Chemistry 1769-1770 (1977).
Etzioni, et al., "Cancer Surveillance Series: Interpreting Trends in Prostate Cancer—Part III: Quantifying the Link Between Population Prostate-Specific Antigen Testing and Recent Declines in Prostate Cancer Mortality," (1999) J. Natl. Canc. Inst., vol. 91, pp. 1033-1039.
European Patent Office Communication pursuant to Article 94(3) EPC dated Apr. 10, 2014, in corresponding Application No. 11 776 745.9 (5 pages).
European Seach Report & Opinion, dated Oct. 2, 2012, EP Application No. 12168495.5.
FDA Drug Information Page—Plenaxis (abarelix for injectable suspension); http://www.fda.gov/cder/drug/infopage/planaxis/default.htm. (Feb. 2004).
fda.gov, Label for Degarelix for injection (Dec. 24, 2008), available at www.accessdata.fda.gov/drugsatfda_docs/label/2008/022201lbl.pdf, last visited Jun. 4, 2013.
Ferlay,et al., "Estimates of the cancer incidence and mortality in Europe in 2006," Annals of Oncology, vol. 18, pp. 581-592 (2007).

(56) References Cited

OTHER PUBLICATIONS

Fleming, et al., "Post-therapy changes in PSA as an outcome measure in prostate cancer clinical Trials," (2006) Nature Clinical Practice Oncolology, vol. 3, No. 12, pp. 658-667.
Forbes, et al., "FDA's Adverse Drug Reaction Drug Dictionary and Its Role in Post-Marketing Surveillance," (1986) Drug Inf. J., vol. 20, pp. 135-145.
Frampton et al., "Degarelix", ADIS International, Drugs, 69 (14): 1967-1976 (2009).
Garnero, "Markers of bone turnover in prostate cancer," Cancer Treatment Reviews, pp. 187-192: 27: 2001.
Garnick M et al: "217 Increase in the electrocardiographic QTC interval in men with prostate cancer undergoing androgen deprivation therapy: Results of three randomized controlled clinical studies", European Urology Supplements, vol. 3, No. 2, Feb. 1, 2004 (Feb. 1, 2004), p. 57, XP027186629, ISSN: 1569-9056.
Gerlinger, et al.,"Recommendation for Confidence interval and sample size calculations for the Pearl Index," (2003) The European Journal of Contraception and Reproductive Health Care, vol. 8, pp. 87-92.
Gillum, T., "The Merck Regulatory Dictionary: A Pragmatically Develop Drug Effects Vocabulary," (1989) Drug Info. J., vol. 23, pp. 217-220.
Gittelman et al., "A 1-Year, Open Label, Randomized Phase II Doe Finding Study of Degarelix for the Treatment of Prostate Cancer in North America," The Journal of Urology, vol. 80, pp. 1986-1992, Nov. 2008.
Gittelman et al: "MP-08.21: A multicentre, randomised one year dose-finding study of degarelix, a gonadotrophin-releasing hormone (GnRH) receptor blocker in prostate caner patients" Urology, Belle Mead, NJ, US vol. 70 No. 3, Sep. 1, 2007 (Sep. 1, 2007)pp. 83-84, XP022248654 ISSN:0090-4295.
Gonzalez-Barcena D et al: "Luteinzing hormone-releasing hormone hormone antagonist centrorelix as primary single therapy in patients with advanced prostatic cancer and paraplegia due to metastatic invasion of spinal cord." Urology Feb. 1995, vol. 45, No. 2, Feb. 1995 (Feb. 1995), pp. 275-281, XP02527258 ISSN: 0090-4295.
Granfors, et al., "Combined Orchiectomy and External Radiotherapy Versus Radiotherapy Alone for Nonmetastatic Prostate Cancer With or Without Pelvic Lymph Node Involvement: A Prospective Randomized Study," J. Urol., (1998), 159:2030-34.
Hackman, et al., "Emerging Risk Factors for Atheroslerotic Vascular Disease," (2003), JAMA, vol. 290, pp. 932-940.
Hegele et al., "Biochemical Markers of Bone Turnover in Patients with Localized and Metastasized Prostate Cancer," Journal Compilation, vol. 99, pp. 330-334, Sep. 7, 2006.
Heidenreich et al., "Welche Mechanismen Liegen Der Besseren Kontrolle Des Psa-Progressionsfreien Uberlebens Von Degarelix Im Vergleich Mit Leuprorelin Zugrunde?", RWTH, Aache, Ferring Arzneimittel GmbH, Kiel, 4 pages.
Hellerstedt, et al., "The Current State of Hormonal Therapy for Prostate Cancer," CA A Cancer Journal for Clinicians, vol. 52, pp. 154-179. (2002).
Huirne J A et al: "Gonadotropin-releasing-hormone-receptor antagonists" Lancet the, Lancet Limited. London, GB, vol. 358, No. 9295, Nov. 24, 2001 (Nov. 24, 201), pp. 1793-1803, XP04805574 ISSN: 0140-6736.
International Search Report dated Sep. 12, 2002, in Application No. PCT/GB02/03116.
Isidro-Llobet et al., "Amino Acid-Protecting Groups," Chem. Rev, pp. 2455-2504, 2009.
Iversen et al., "Improved outcomes with degarelix monotherapy compared with luteinizing hormone-releasing hormone (LHRH) agonists plus antiandrogen in the treatment of men with advanced prostate cancer", 29th Congress of the Scandinavian Association of Urologiest, May 22, 2013, 2 pages.
Iversen et al: "MP-08.18" Urology, Belle Mead, NJ, US, vol. 68, Nov. 1, 2006 (Nov. 1, 2006), p. 102, XP05709326 ISSN 0090-4295.
Jiang et al., "Betidamino Acid-Scan of the GNRH Antagonist Acyline," Journal of Medicinal Chemistry, American Chemical Socitey, Washington, US, vol. 40, 1997, pp. 3739-3748.
Jiang, et al.,"GnRH Antagonists: A New Generation of Long Acting Analogues Incorporating p-Ureido-phenylalanies at Positions 5 and 6," (2001) J. Med. Chem., vol. 44, pp. 453-467.
Keating Nancy L et al: "Diabetes and cardiovascular disease during androgen deprivation therapy for prostate cancer." Journal of Clinical Oncology: Official Journal of the American Society of Clinical Oncology Sep. 20, 2006, vol. 24, No. 27, Sep. 20, 2006 (Sep. 20, 2006), pp. 4448-4456, XP002687918, ISSN: 1527-7755.
Kirk et al., "Immediate Versus deferred treatment for advanced prostatic cancer; initial results of the Medical Research Counsel trial.," British Journal of Urology, (1997) vol. 79, pp. 235-246.
Lehmann, "Testing Statistical Hypotheses," (1986) Second Edition, John Wiley & Sons, New York, ISBN 0-471-84083-1.
Lilja, et al., "Prostate-specific antigen and prostate cancer: prediction, detection and monitoring," (2008) Nature Reviews/Cancer, vol. 8, pp. 268-278.
Lukka, et al., "Maximal androgen blockade for the treatment of metastatic prostate cancer—a systematic review," Current Oncology, vol. 13, No. 3, pp. 81-93. (2006).
Lyseng-Williamson, Katherine A., "Degarelix: a guide to its use in advanced prostate cancer," 28(5) Drugs Ther. Perspect. 6-10 (2012).
Malkin, "Are techniques used for intramuscular injection based on research evidence?" nursingtimes.net, Nursing Times; 104; 50/51, 48-51 Dec. 16, 2008.
Manning et al., "Stability of Protein Pharmaceuticals: An Update," Pharmaceutical Research, vol. 27, No. 4, pp. 544-575, Apr. 2010.
McNeil, et al., "On the Elicitation of Preferences for Alternative Therapies," (1982) N. Engl. J. Med., vol. 306, No. 21, pp. 1259-1262.
MedDRA website, http://www.meddramsso.com. (2009).
Messing, et al., "Immediate Hormonal Therapy Compared with Observation after Radical Prostatectomy and Pelvic Lyphadenectomy in Men with Node-Positive Prostate Cancer," (1999), N. Eng. J. Med., vol. 341, pp. 1781-1788.
Miller et al., Differential outcomes from an analysis of six comparative randomised clinical trials of degarelix versus luteinising hormone-releasing hormone (LHRH) agonists) (2012).
Miller et al., "Disease control-related outcomes from an analysis of six comparative randomised clinical trials of degarelix versus luteinising hormone-releasing hormone (LHRH) agonists," (2012).
Mongiat-Artus P et al: "Role of Luteinising Hormone Releasing Hormone (LHRH) Agonists and Hormonal Treatment in the Management of Prostate Cancer" European Urology Supplements, vol. 4, No. 5, Jul. 1, 205 (Jul. 1, 2005), pp. 4-13, XP004926296 ISSN: 1569-9056.
Mongiat-Artus, et al., "Abarelix: the first gonadotrophin-releasing hormone antagonist for the treatment of prostate cancer," (2004), Expert Opin. Pharmacother, vol. 5, pp. 2171-2179.
Montalbetti et al., "Amide bond formation and peptide coupling," Science Direct (Tetrahedron 2005), pp. 10827-10852.
National Cholesterol Education Program (NCEP) Guidelines for Interpretation of Lipid Values, (2001; updated 2004) XP-02729834.
NCEP ATP III Classification of Total Cholesterol, LDL-C, and HDL-C, XP-02729835 (2003 first publication; 2010).
Notice of Third Party Opposition, filed on Jan. 23, 2015, in EP 2249859.
Office Action (final) dated Feb. 8, 2017, U.S. Appl. No. 14/747,218.
Office Action (final) dated Jan. 2, 2019, U.S. Appl. No. 15/205,108.
Office Action (final) dated Jan. 29, 2015, U.S. Appl. No. 12/155,897.
Office Action (final) dated Jan. 29, 2016, U.S. Appl. No. 12/901,270.
Office Action (final) dated Jan. 9, 2014, U.S. Appl. No. 12/829,467.
Office Action (final) dated Jul. 14, 2016, U.S. Appl. No. 14/454,825.
Office Action (final) dated Mar. 10, 2016, U.S. Appl. No. 14/139,922.
Office Action (final) dated Mar. 24, 2016, U.S. Appl. No. 13/458,330.
Office Action (final) dated Mar. 5, 2014, U.S. Appl. No. 12/155,897.
Office Action (final) dated Mar. 6, 2014, U.S. Appl. No. 12/901,270.
Office Action (final) dated Oct. 8, 2013, U.S. Appl. No. 13/381,762.
Office Action (final) dated Sep. 12, 2017, U.S. Appl. No. 12/901,270.
Office Action (final) dated Apr. 8, 2016, U.S. Appl. No. 14/403,775.

(56) References Cited

OTHER PUBLICATIONS

Office Action (Final) dated May 20, 2014, in co-pending U.S. Appl. No. 13/458,330.
Office Action (non-final) dated Apr. 7, 2017, U.S. Appl. No. 12/368,935.
Office Action (non-final) dated Feb. 19, 2016, U.S. Appl. No. 14/454,825.
Office Action (non-final) dated Jun. 16, 2016, U.S. Appl. No. 14/747,218.
Office Action (non-final) dated Jun. 30, 2015, U.S. Appl. No. 13/458,330.
Office Action (non-final) dated Jun. 5, 2015, U.S. Appl. No. 12/155,897.
Office Action (non-final) dated Jun. 4, 2015, U.S. Appl. No. 14/139,922.
Office Action (non-final) dated Jun. 5, 2015, U.S. Appl. No. 12/901,270.
Office Action (non-final) dated Sep. 3, 2015, U.S. Appl. No. 14/403,775.
Office Action dated Apr. 10, 2018, U.S. Appl. No. 12/901,270.
Office Action dated Dec. 19, 2017, U.S. Appl. No. 15/420,156.
Office Action dated Jul. 25, 2013, U.S. Appl. No. 12/829,467.
Office Action dated Jul. 26, 2013, U.S. Appl. No. 12/901,270.
Office Action dated Jun. 11, 2013, U.S. Appl. No. 13/381,762.
Office Action dated Jun. 28, 2018, U.S. Appl. No. 15/405,552.
Office Action dated Jun. 6, 2013, U.S. Appl. No. 12/774,113.
Office Action dated Mar. 26, 2018, U.S. Appl. No. 15/205,108.
Office Action dated May 5, 2015, U.S. Appl. No. 13/881,751.
Office Action dated Nov. 1, 2018, U.S. Appl. No. 12/901,270.
Office Action dated Sep. 11, 2013, in U.S. Appl. No. 12/771,199.
Office Action dated Sep. 3, 2013, in U.S. Appl. No. 13/458,330.
Office Action dated Apr. 2, 2012, in U.S. Appl. No. 12/368,935.
Office Action dated Aug. 27, 2014 in U.S. Appl. No. 13/881,744.
Office Action dated Dec. 3, 2013, in U.S. Appl. No. 12/368,713.
Office Action dated Jan. 31, 2013, in U.S. Appl. No. 12/901,270.
Office Action dated Mar. 26, 2018, in U.S. Appl. No. 15/205,108.
Office Action dated Jan. 2, 2019, in U.S. Appl. No. 15/205,108.
Office Action dated Mar. 1, 2011, in U.S. Appl. No. 12/368,713.
Office Action dated Mar. 30, 2017, in U.S. Appl. No. 14/454,825.
Office Action dated Mar. 8, 2011, in U.S. Appl. No. 12/155,897.
Office Action dated Oct. 12, 2011, in U.S. Appl. No. 12/155,897.
Office Action dated Oct. 2, 2014, in U.S. Appl. No. 12/829,467.
Office Action dated Oct. 22, 2009, in U.S. Appl. No. 12/155,897.
People's Republic of China First Office Action dated Feb. 25, 2013 in corresponding Application No. 201080019696.2, 2 pages.
Persad, "Leuprorelin Acetate in Prostate Cancer: A European Update," (2002) Int. J. Clin. Pract., vol. 56, No. 5, pp. 389-396.
Ramaswamy et al., "Serum Levels of Bone Alkaline Posphatase in Breast and Prostate Cancers with Bone Metastasis," Indian Journal of Clinical Biochemistry, pp. 110-113, 15(2), 2000.
Romero-Corral, et al., "Association of bodyweight with total mortality and with cardiovascular events in coronary artery disease: a systematic review of cohort studies," (2006) Lancet, 368:666-678.
Saltzman, A., "Adverse Reaction Terminology Standardization: A Report on Schering-Plough's Use of the WHO Dictionary and the Formation of the WHO Adverse Reaction Terminology Users Group (WUG) Consortium," (1985) Drug Info. J., vol. 19, pp. 35-41.
Samant et al., "Novel analogues of degarelix incorporating hydroxy-, methoxy- and pegylated-urea moieties at postions 3, 5, 6 and the N-terminus," J. Med Chem. 49(12), pp. 3536-3543, 2006.
Schwach et al., "Biodegradable PLGA microparticles for sustained release of a new GnRH antagonist . . . ," European Journal of Pharmaceutics and Biopharmaceuticals, May 1, 2004, vol. 57, No. 3, pp. 441-446.
Schwach G. et al: "Biodegradable microparticles for sustained release of a new GnRH antagonist—part I: screening commercial PLGA and formulation technologies", European Journal of Pharmaceutics and Biopharmaceuticals, Elsevier Science Publishers B.V., Amsterdam, NL, vol. 56, No. 3, Nov. 1, 2003, pp. 327-336.

SEER Program and the National Center for Health Statistics, <http://seer.cancer.gov/.> (2000; 2005).
Sharma et al., "To scale or not to scale: the principles of does extrapolation," British Journal of Pharmacology, pp. 907-921, 2009.
Smith et al., "Cardiovascular Safety of Degarelix: Results From a 12-Month, Comparative, Randomized, Open Label, Parallel Group Phase III Trial in Patients With Prostate Cancer," 184 The Journal of Urology 2313-2319 (2010).
Smith, M.R. et al., "Gonadotropin-Releasing Hormone Blockers and Cardiovascular Disease Risk: Analysis of Prospective Clinical Trials of Degarelix," 186 The Journal of Urology 1835-1842 (2011).
Sorbera et al., "Degarelix Acetate", GnRH Antagonist Prostate Cancer Therapy; Drugs of the Future 2006, vol. 31, No. 9, pp. 755-766.
Spilker, Bert, "Guide to Cinical Trials," (1991) Raven Press, Ltd., New York, ISBN 0-88167-767-1.
Spilker, Bert, "Quality of Life and Pharmacoeconomics in Clinical Trials," (1996) Lippincott-Raven Publishers, New York, ISBN 0-7817-0332-8.
Steinberg, et al., "Degarelix: A Gonadotropin-Releasing Hormone Antagonist for the Management of Prostate Cancer," Clinical Therapeutics, vol. 31, pp. 2312-2331, 2009.
Stephens, M.D.B., "The Detection of New Adverse Drug Reactions," (1988) Stockton Press, New York, ISBN 0-333-45417-0.
Teal, et al., "Adverse Drug Experience Management: A Brief Review of the McNeil Pharmaceutical System," (1985) Drug Info. J., vol. 19, pp. 17-25.
The K-Zone, Biophysical data tables: standard man, Jul. 2004; printed Mar. 14, 2009 from www.kevinboone.com/biodat_stdman.html; 1 page.
Thompson, et al., "Sudden Death to Disease Flare With Luteinizing Hormone-Releasing Hormone Agonist Therapy for Carcinoma of the Prostate," J. Urol., (1990) vol. 144, pp. 1479-1480.
Tsai Henry K et al: Androgen deprivation therapy for localized prostate cancer and the risk of cardiovascular mortality., Journal of the National Cancer Institute Oct. 17, 2007 LNKD—PUBMED:17925537, vol. 99, No. 20, Oct. 17, 2007 (Oct. 17, 2007), pp. 1516-1524, XP002687919, ISSN: 1460-2105.
Turner, et al., "The Processing of Adverse Reactoin Reports at FDA," (1986) Drug. Inf. J., vol. 20, pp. 147-150.
Van Kerrebroeck et al., "Desmopressin in the Treatment of Nocturia: A Double-Bind, Placebo-Controlled Study", European Urology, 52, (Jan. 16, 2007).
Van Poppel et al., "A One-Year, Multicentre, Randomised Study of Degarelix a Gonadatrophin-Releasing Hormone (GNRH) Receptor Blocker, in Prostate Cancer Patients," Eur Urol Supppl 2005:5(2):251.
Van Poppel et al., "Degarelix: A Novel Gonadotropin-Releasing Hormone (GnRH) Receptor Blocker—Results from a 1-yr, Multicentre, Randomised, Phase 2 Dosage-Finding Study in the Treatment of Prostate Cancer", European Urology No. 54, pp. 805-815 (2008).
Van Poppel H et al: "23 Long-Term Evaluation of Degarelix, a Gonadotrophin-Releasing Hormone (GNRH) Receptor Blocker, Investigated in a Multicentre Randomised Study in Prostate Cancer (CAP) Patients" European Urology Supplements, vol. 6, No. 2, Mar. 1, 2007 (Mar. 1, 2007), p. 28, XP022686644 ISSN: 1569-9056 [retrieved on Mar. 1, 2007].
Van Poppel, "Evaluation of degarelix in the management of prostate cancer," Cancer Management and Research, vol. 2, pp. 39-52, 2010.
Versuchsbericht Zerfallzeit Ursprunglicher Dateiname:D13,Beigefugt als:Other-evidence-1 (Jul. 23, 2014).
Wiegel et al., "Neoadjuvant Androgen Deprivation Therapy for Prostate Volume Reduction, Lower Urinary Tract Symptom Relief and Quality of Life Improvement in Men with Intermediate- to High-risk Prostate Cancer: A Randomised Non-inferiority Trial of Degarelix versus Goserelin plus Bicalutamide", 2 pages.
Wilson, et al., "Leuprolide acetate: a drug of diverse clinical applications," Expert Opin. Investig. Drugs, (2007), vol. 16, pp. 1851-1863.
Wilson, et al., "Prediction of Coronary Heart Disease Using Risk Factor Categories," (1998) Circulation, 97:1837-47.
Wolff et al., "Cumulative analysis from six comparative randomised clinical trials of degarelix versus luteinising hormone-releasing

(56) References Cited

OTHER PUBLICATIONS hormone (LHRH) agonists: Better PSA-progressionfree survival confirmed in trials an everyday practice", Gerring Arzneimittel GmbH, Kiel, 2 pages.

Yannucci, et al., "The Effect of Androgen Deprivation Therapy on Fasting Serum Lipid and Glucose Parameters," (2006) J. Urol., vol. 176, pp. 520-525.

First Examination Report from the Intellectual Property Office of India dated Aug. 21, 2019, 7 pages.

EMEA, European Medicines Agency, "Assessment Report for Firmagon", Doc. Ref., EMEA/CHMP/635761/2008, pp. 1-67.

Kevin K.-C. Liu, Subas M. Sakya, Christopher J. O'Donnell, Andrew C. Flick, and Jin Li, "Synthetic Approaches to the 2009 New Drugs", Biorganic and Medicinal Chemistry 19, (2011), pp. 1136-1154.

Ferring BV. "GnRH Antagonists", Indian Granted Patent IN224650, based on PCT Application WO9846634 A, pp. 1-43, (Dec. 5, 2008).

\* cited by examiner

MANUFACTURE OF DEGARELIX

This is a continuation of application Ser. No. 15/420,156, filed Jan. 31, 2017 (now U.S. Pat. No. 10,172,906 B2, issued Jan. 8, 2019), which is a continuation of application Ser. No. 14/403,775, filed Nov. 25, 2014 (now U.S. Pat. No. 9,592,266 B2, issued on Mar. 14, 2017), which is a national stage application under 35 U.S.C. § 371 of International Application No. PCT/EP2013/061264, filed May 31, 2013, which claims priority of European Patent Application No. 12170454, filed Jun. 1, 2012; the contents of each application are incorporated herein by reference.

TECHNICAL FIELD

The present invention relates to a manufacturing process for preparing Degarelix.

BACKGROUND OF THE INVENTION

Prostate cancer is a leading cause of morbidity and mortality for men in the industrialised world. Degarelix, also known as FE200486, is a third generation gonadotropin releasing hormone (GnRH) receptor antagonist (a GnRH blocker) that has been developed and approved for prostate cancer patients in need of androgen ablation therapy (Doehn et al., Drugs 2006, vol. 9, No. 8, pp. 565-571; WO 09846634). Degarelix acts by immediate and competitive blockade of GnRH receptors in the pituitary and, like other GnRH antagonists, does not cause an initial stimulation of luteinizing hormone production via the hypothalamic-pituitary-gonadal axis, and therefore does not cause testosterone surge or clinical flare (Van Poppel, Cancer Management and Research, 2010:2 39-52; Van Poppel et al., Urology, 2008, 71(6), 1001-1006; James, E. F. et al., Drugs, 2009, 69(14), 1967-1976).

Degarelix is a synthetic linear decapeptide containing seven unnatural amino acids, five of which are D-amino acids. It has ten chiral centers in the back bone of the decapeptide. The amino acid residue at position 5 in the sequence has an additional chiral center in the side-chain substitution giving eleven chiral centers in total. Its CAS registry number is 214766-78-6 (of free base) and it is commercially available under the Trademark Firmagon™. The drug substance is chemically designated as D-Alaninamide, N-acetyl-3-(2-naphthalenyl)-D-alanyl-4-chloro-D-phenylalanyl-3-(3-pyridinyl)-D-alanyl-L-seryl-4-[[[(4S)-hexahydro-2,6-dioxo-4-pyrimidinyl]carbonyl]amino]-L-phenylalanyl-4-[(aminocarbonyl)amino]-D-phenylalanyl-L-leucyl-N6-(1-methylethyl)-L-lysyl-L-prolyl- and is represented by the chemical structure below (in the following also referred to as Formula I):

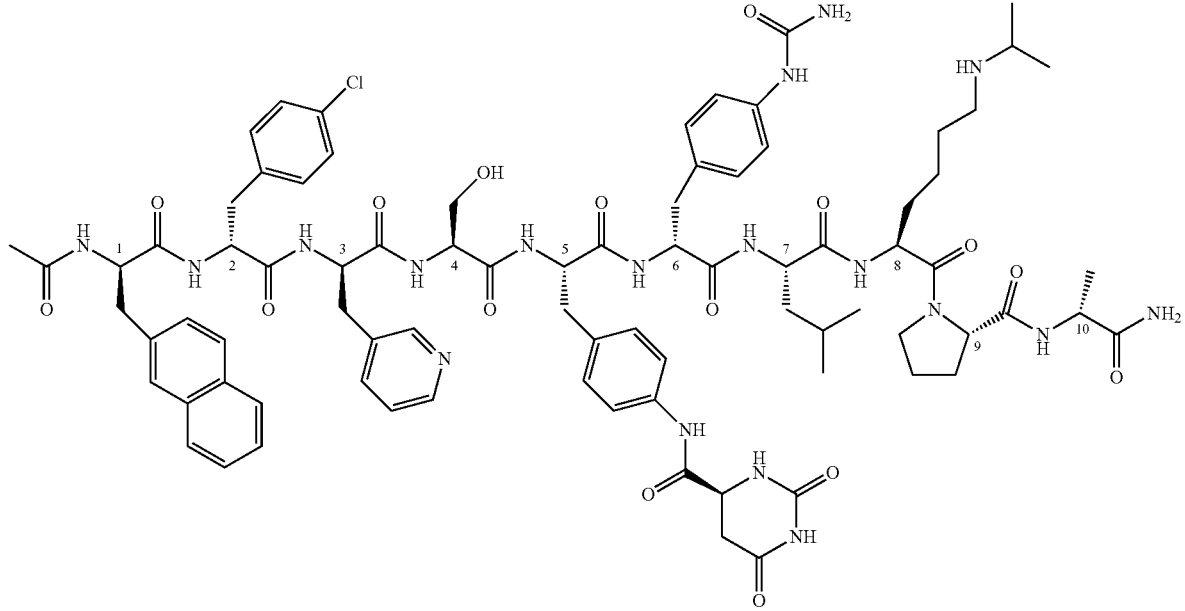 [SMILES: CC(=O)N[C@H](Cc1ccc2ccccc2c1)C(=O)N[C@H](Cc1ccc(Cl)cc1)C(=O)N[C@H](Cc1cccnc1)C(=O)N[C@@H](CO)C(=O)N[C@@H](Cc1ccc(NC(=O)[C@@H]2CC(=O)NC(=O)N2)cc1)C(=O)N[C@H](Cc1ccc(NC(N)=O)cc1)C(=O)N[C@@H](CC(C)C)C(=O)N[C@@H](CCCCNC(C)C)C(=O)N1CCC[C@H]1C(=O)N[C@H](C)C(N)=O]

The structure of Degarelix can also be represented as:

Ac-D-2Nal-D-4Cpa-D-3Pal-Ser-4Aph(L-Hor)-D-4Aph(Cbm)-Leu-Lys(iPr)-Pro-D-Ala-NH$_2$ where Ac is acetyl, 2Nal is 2-naphthylalanine, 4Cpa is 4-chlorophenylalanine, 3Pal is 3-pyridylalanine, Ser is serine, 4Aph is 4-aminophenylalanine, Hor is hydroorotyl, Cbm is carbamoyl, Leu is leucine, Lys(iPr) is N6-isopropyllysine, Pro is proline and Ala is alanine.

For the purposes of describing this invention, each amino acid in Degarelix will be given the shorthand notation as follows:

$AA_1$ is D-2Nal, $AA_2$ is D-4Cpa, $AA_3$ is D-3Pal, $AA_4$ is Ser, $AA_5$ is 4Aph(L-Hor), $AA_6$ is D-Aph(Cbm), $AA_7$ is Leu, $AA_8$ is Lys(iPr), $AA_9$ is Pro and $AA_{10}$ is D-Ala.

Thus, Degarelix can be represented as Ac-$AA_1$-$AA_{10}$-$NH_2$.

Degarelix has previously been prepared using Boc-solid phase peptide synthesis (SPPS) methodology as reported in WO 98/46634 and Jiang et al., J. Med. Chem. 2001, 44, 453-467.

WO2010/12835 and WO2011/066386 describe the preparation of degarelix using an Fmoc strategy. WO2012/055905 and WO2012/055903 describe liquid phase syntheses of degarelix.

SUMMARY OF THE INVENTION

The physicochemical characterization of degarelix has shown that this decapeptide has the ability to self-associate, and eventually form gels in aqueous solution. Self-aggregation makes this compound build-up a depot in situ when injected subcutaneously or intramuscularly. The degarelix depot was shown to provide a sustained release of the active over months depending on the dosage. At present, the drug is administered in dosages of 120 mg (40 mg/ml) for first injection, and of 80 mg (20 mg/ml) for sustained release over one month.

The present inventors have surprisingly found that viscosity, and hence sustained release properties and bioavailability, of the reconstituted drug product can be controlled through processing of the crude peptide (e.g. obtained by Fmoc strategy, liquid phase synthesis or another route) into the drug substance. The viscosity associated with the drug substance surprisingly correlates with the viscosity associated with the drug product, even after a further reconstitution and lyophilisation. The viscosity of the drug product has to be controlled within a range of up to 15 mPas, preferably within a range of 2 to 12 mPas, to obtain the desired depot formation and thus sustained release. The present invention provides processes that allow the manufacture of drug products that show this viscosity, as determined upon reconstitution with the reconstitution fluid at a concentration of 20 mg degarelix per ml reconstitution fluid.

In a first aspect, the present invention thus provides a method for controlling the viscosity of a degarelix product to be no greater than 15 mPas, preferably within a range of 2 to 12 mPas, as determined upon reconstitution with water for injection in an amount of 20 mg degarelix free base/ml, comprising the steps of:
1. Providing a lyophilized degarelix drug substance which shows a viscosity of up to 3.2 mPas, as determined upon dissolution in water containing mannitol (2.5% w/V) in an amount of 20 mg degarelix free base/ml
2. Dissolving the lyophilized degarelix drug substance in mannitol-containing water to provide an aqueous degarelix-mannitol mixture;
3. Lyophilizing the aqueous degarelix-mannitol mixture to provide the degarelix drug product.

In a second aspect, the present invention provides a method for producing a lyophilized degarelix product which shows a viscosity of up to 15 mPas, preferably within a range of 2 to 12 mPas, as determined upon reconstitution with water for injection in an amount of 20 mg degarelix free base/ml, comprising the steps of:
1. Providing a lyophilized degarelix drug substance which shows a viscosity of up to 3.2 mPas, as determined upon dissolution in water containing mannitol (2.5% w/V) in an amount of 20 mg degarelix free base/ml
2. Dissolving the lyophilized degarelix drug substance in mannitol-containing water to provide an aqueous degarelix-mannitol mixture; and
3. Lyophilizing the aqueous degarelix-mannitol mixture to provide the degarelix drug product.

In a third aspect, the present invention provides a method for producing degarelix drug product comprising a lyophilized degarelix drug product and a liquid for reconstitution (reconstitution fluid) which, upon reconstitution with said liquid in an amount of 20 mg degarelix free base/ml, shows a viscosity of up to 15 mPas, preferably within a range of 2 to 12 mPas, comprising the steps of:
1. Dissolving a lyophilized degarelix drug substance in a mannitol containing aqueous solution to provide a degarelix-mannitol mixture;
2. Lyophilizing the degarelix-mannitol mixture to provide the degarelix drug product, wherein a viscosity-reducing agent is added to the degarelix-mannitol mixture prior to lyophilization.

The present invention also provides a lyophilized degarelix drug substance which shows, upon dissolution in water containing 2.5 wt. % mannitol in an amount of 20 mg degarelix free base/ml, a viscosity of up to 3.2 mPas, and processes for providing this lyophilized degarelix drug substance.

Moreover, the present invention provides a degarelix drug product comprising a lyophilized degarelix drug product and a reconstitution fluid which, upon reconstitution with said reconstitution fluid in an amount of 20 mg degarelix free base/ml, shows a viscosity of up to 15 mPas, preferably within a range of 2 to 12 mPas, and contains a viscosity-reducing agent in an amount of 0.001 to 5 mg/ml.

FIGURES

FIG. 1 shows the relationship between drug substance viscosity and drug product viscosity.

Figure 2:
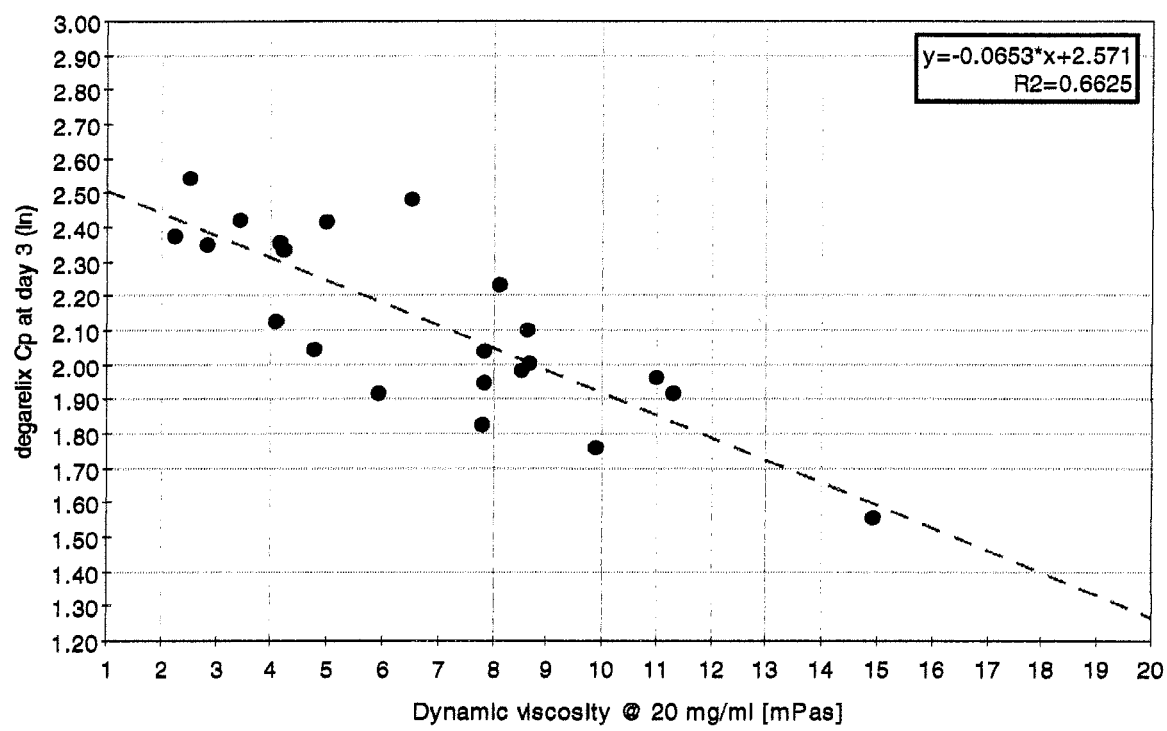
Figure 3:
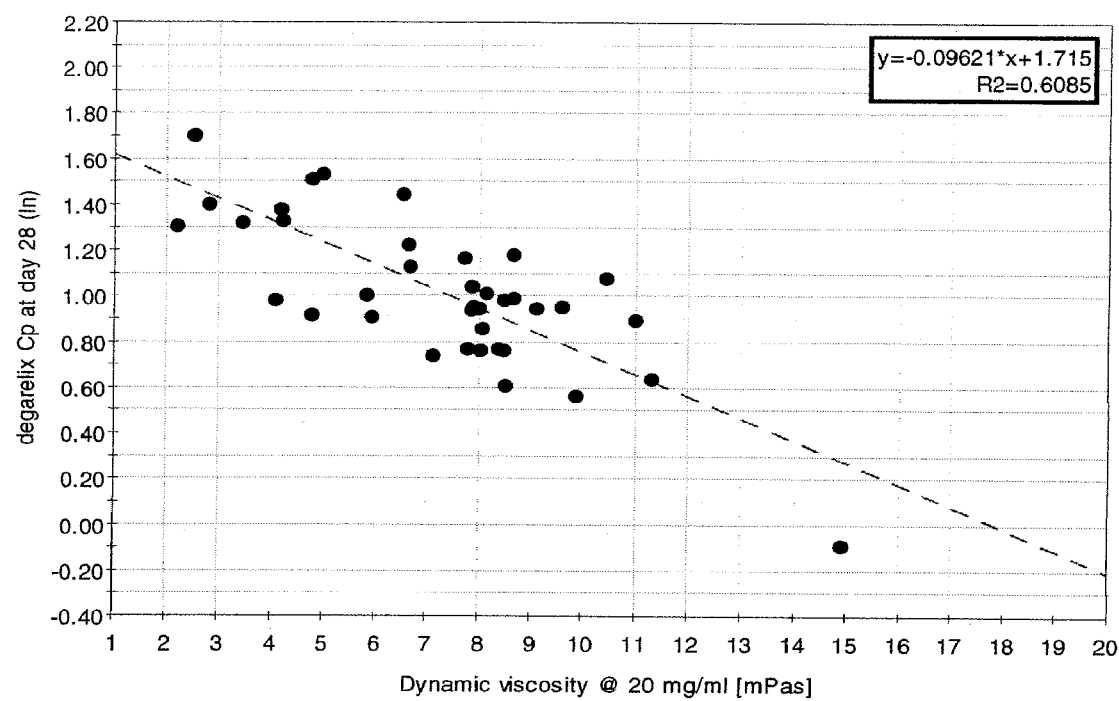

FIGS. 2 and 3 show the relationship between dynamic viscosity of degarelix dosing suspension (20 mg/ml) and degarelix plasma concentrations (rat) at day 3 (FIG. 2) and day 28 (FIG. 3).

DETAILED DESCRIPTION OF THE INVENTION

The methods for producing a lyophilized degarelix product both according to the first and the second aspect start with the degarelix drug substance which will be described in more detail.

The Degarelix Drug Substance

The decapeptide degarelix can be prepared by solid phase peptide synthesis, as disclosed in WO98/46634, WO2010/12835 and WO2011/066386, or by liquid phase peptide synthesis, as disclosed in WO2012/055905 or WO2012/055903. This peptide synthesis provides crude degarelix which is further purified and then lyophilized to provide a lyophilized product which consists of degarelix, acetic acid, a residual amount of water, and minor amounts of impurities due to the production process, if any. This product is referred to as degarelix drug substance or merely drug substance in the present invention. The degarelix drug substance preferably consists of degarelix, 4.5 to 10 wt. % acetic acid (w/w), and up to 10 wt. % water (w/w).

The manufacture of the drug substance can be divided into a first step (A) providing purified degarelix in solution, and a second step (B) providing the degarelix drug substance.

Step (A): Purification

Step (A) comprises the purification of crude degarelix in one or more steps, preferably two steps, optionally followed by a column concentration and/or salt exchange step.

Crude degarelix, as obtained by LPPS or SPPS, is first subjected to purification. The purification is preferably carried out by applying the peptide solution obtained by SPPS or LPPS to a column with reversed phase material, which is preferably pre-equilibrated with buffer. This first purification step preferably provides a purity of at least 95%, as determined by HPLC.

In a preferred embodiment, the reverse phase column chromatography is repeated to obtain a product with purity of at least 97.5%, as determined by HPLC.

In a particularly preferred embodiment, the purified degarelix solution with a purity of at least 95%, preferably at least 97.5%, is subjected to further column chromatography step to pre-concentrate the degarelix solution and/or for salt exchange (particularly if acetic acid is used for pH adjustment of the eluents in the last purification step).

This pre-concentration and/or salt exchange step is also preferably carried out on a reverse phase column: The purified degarelix solution is diluted with water (preferably 1.5 to 2.5 times) and applied to the column, pre-equilibrated with buffer. The column is preferably first washed with ethanol (low concentration, generally below 20%) and aqueous ammonium acetate and subsequently with ethanol (low concentration, generally below 20%)/acetic acid/water. The column is then eluted, e.g. with ethanol (high concentration, generally 20 to 60%)/acetic acid/water to obtain a more concentrated solution of degarelix compared to the solutions after the purification step(s). The process is not limited to ethanol as an organic modifier in the eluent. Other solvents such as acetonitrile can also be used.

Step (A) provides purified degarelix in solution.

Step (B)

The subsequent treatment of the purified degarelix in solution to obtain the degarelix drug substance can be carried out in different ways. In the following, four preferred ways are illustrated (Steps (B1), (B2), (B3), and (B4)).

Step (B1): Concentration-De-aggregation-Lyophilization

The purified degarelix in solution is first subjected to a concentration step in which ethanol or another organic modifier such as acetonitrile is removed by evaporation. This step is preferably carried out with a rotavap evaporator. The preferred maximum temperature during evaporation is 40° C. The resulting highly concentrated, viscous degarelix product (aggregated product that is usually in gel form) is then treated with acetic acid (de-aggregation step), preferably filtered, and lyophilized.

The de-aggregation step is important to control the viscosity of the drug substance. Therefore, the de-aggregation step is preferably carried out with one or more, most preferably all of the following conditions:

Final acetic acid concentration: 6-40%, preferably 15-35% (v/v)
Temperature 0 to 35° C., preferably 2 to 30° C., most preferably 5 to 15° C.
Degarelix concentration (free base) 5-35 g/l, preferably 10-20 g/l
Time 1-15 hours Within these limits, suitable combinations of process parameters can be found by simple experimentation.

The lyophilization step is preferably carried out at an ice thickness of 1.2 to 2.4 cm and a secondary drying time of 1 to 17 hours. The secondary drying temperature is usually around 20° C. (15 to 25° C.).

In a preferred embodiment, step (B1) thus provides a lyophilized drug substance that shows a viscosity of less than 3.2 mPas, preferably between 1.15 and 2 mPas (as determined upon dissolution in an amount of 20 mg degarelix free base in 1 ml of water, containing 2.5% (w/V) mannitol). The method for measuring the viscosity is described in the experimental section. A drug substance fulfilling this viscosity requirement is further referred to as drug substance (1), whereas a drug substance not fulfilling this viscosity requirement is further referred to as drug substance (2). Drug substance (2) has a preferred viscosity of 3.2 to 15 mPas, upon dissolution in an amount of 20 mg in 1 ml water. Drug substance (2) may even be gel-like, in a condition of significantly more than 3.2 mPas, even though its viscosity cannot be measured precisely.

In this respect, it is noted that "upon dissolution in an amount of 20 mg in 1 ml of water" merely refers to the conditions for measuring the viscosity and does not mean that the drug substance is present in a solution of 20 mg/ml. Most preferably, the drug substance is present in lyophilized form.

The drug substance, in particular drug substance (1), is preferably further characterized by an acetic acid content of 4.5 to 10.0% (w/w) and/or a water content of 10% or less (w/w). Additionally, the drug substance, in particular drug substance (1), preferably shows an optical density of 0.10 AU or less (at a concentration of 20 mg degarelix free base/ml in 2.5% mannitol (aq)). The method for measuring the optical density is described in the experimental section.

Thus, the invention provides a method for producing the degarelix drug substance (1), comprising the steps of:

a. Purifying degarelix as obtained by liquid or solid phase peptide synthesis to obtain a degarelix solution with a purity of at least 95%;
b. Evaporating solvent to concentrate the degarelix solution to obtain aggregated degarelix;
c. Deaggregating the aggregated degarelix with acetic acid; and
d. Lyophilizing the deaggregated degarelix to provide the degarelix drug substance.

The invention further provides a method for modulating the viscosity of degarelix, such that following lyophilization and reconstitution with water, the viscosity of a 20 mg/ml degarelix solution in 2.5% w/V mannitol is no greater than 15 mPas, comprising:

treating aggregated degarelix with acetic acid; and
lyophilizing the mixture of degarelix and acetic acid.

In certain embodiments, the conditions for acetic acid addition and lyophilization are as described above. In particular embodiments, the acetic acid content following lyophilization is 4.5 to 10.0% (w/w).

Step (B2): Column Concentration—Lyophilization

The degarelix solution obtained in step A (preferably after a one- or two-step purification method, e.g. without pre-concentration/salt exchange) is loaded onto a chromatographic column, ion exchange is performed and the column is rinsed (washed) with diluted acetic acid (about 1%). Degarelix is eluted from the column using aqueous acetic acid at a AcOH concentration of 20 to 50 wt. %, preferably 23 to 37 wt. %, preferably 23 to 27 wt. %, preferably 27 to 37 wt. %, preferably 33 to 37 wt. %, preferably 35 wt. %, and subsequently optionally diluted to appropriate AcOH concentration, filtered. Then, the AcOH/water solution of degarelix is lyophilized. The stationary phase in the column can be of different types. The stationary phase can contain functional groups like hydrocarbons (aliphatic and aromatic), alcohols, nitriles, groups with appropriate acid/base properties and ion-exchange groups but is not limited to this type of groups. This process provides the drug substance, preferably drug substance (1).

Thus, the invention also provides a method for producing the degarelix drug substance, comprising the steps of:

a. Purifying degarelix as obtained by liquid or solid phase peptide synthesis to obtain a degarelix solution with a purity of at least 95%;
b. Loading the degarelix solution onto a chromatographic column;
c. Eluting degarelix from the column with acetic acid to provide eluted degarelix;
d. Lyophilizing the eluted degarelix to provide the degarelix drug substance.

Step (B3) Isolation Via Lyophilization-Reconstitution in AcOH/Water-Lyophilization Purified degarelix in solution obtained after Step A is isolated via lyophilization; the resulting lyophilized product is dissolved at a concentration between 10 and 20 g/L in 2% acetic acid, and lyophilized again to give degarelix drug substance (1).

Step (B4): Spray-Drying

Purified degarelix in solution (EtOH/water containing AcOH or ACN/water containing AcOH obtained after Step A, or as described in Step B1 except for lyophilization, or B2 except for lyophilization) is isolated via spray drying to give degarelix drug substance (1).

In a preferred embodiment, a purified degarelix solution as obtained in step A is directly subjected to the spray-drying process. The AcOH concentration of said aqueous degarelix solution subjected to spray-drying is adjusted to 6 to 40% (v/v), preferably 15 to 35% (v/v).

After having described the manufacture of the drug substance, we will now describe the manufacture of degarelix drug product. The lyophilized degarelix drug product comprises the degarelix drug substance and mannitol, i.e. it comprises (and preferably consists of) degarelix, acetic acid, mannitol, a residual amount of water, and minor amounts of impurities due to the production process, if any.

Production Process a of the Degarelix Drug Product

Production process A is the first aspect of the invention mentioned above, i.e. a method for producing degarelix drug product which, upon reconstitution with water for injection in an amount of 20 mg degarelix free base/ml, shows a viscosity of up to 15 mPas, preferably within a range of 2 to 12 mPas, comprising the steps of:

a. Providing a lyophilized degarelix drug substance, preferably degarelix drug substance (1);
b. Dissolving the lyophilized degarelix drug substance in mannitol-containing water to provide an aqueous degarelix-mannitol mixture;
c. Lyophilizing the aqueous degarelix-mannitol mixture to provide the degarelix drug product.

In the present invention, "upon reconstitution with water for injection in an amount of 20 mg/ml" refers to the conditions for measuring the viscosity and does not mean that the drug product is present in a solution of 20 mg/ml. Most preferably, the drug product is present in lyophilized form, optionally in combination with reconstitution liquid. Preferred amounts per vial are in the range of 60 to 300 mg (such as 120 mg, 80 mg, and 240 mg). Alternatively, it can be provided as reconstituted drug product, with preferred concentrations in the range of 2 to 100 mg/ml, preferably 10 to 70 mg/ml (such as 40 mg/ml, 20 mg/ml, and 60 mg/ml).

Step b may also be referred to as compounding step. In a preferred embodiment, filtration and vial filling are carried out after compounding and before freeze-drying so that the entire preferred production process A comprises the steps of:

Compounding to provide the unfiltered bulk drug product
Filtration (sterile)
Vial filling
Freeze-drying/Lyophilization Compounding to Provide the Bulk Drug Product The drug substance is subjected to a compounding step, which is generally carried out as follows:

For the production of the unfiltered bulk drug product, drug substance and mannitol are dissolved in water (pure water; generally Milli-Q water) each in amounts of 10-60 g, per 1000 g batch size. Typical amounts are 20 to 50 g drug substance (as degarelix free base content as determined by HPLC and 10 to 50 g mannitol per 1000 g. The actual amount depends on the final concentration of degarelix in the drug product and the volume of the reconstitution liquid (mannitol is preferably added such that an isotonic solution with an osmolality of 300 mOsm+/−30 mOsm is obtained after reconstitution).

For production, water (usually approx. 80% of the total amount of water) is added to a compounding vessel. The mannitol is added and dissolved by stirring. Then the drug substance is added to the stirred mannitol solution and the formulated bulk (batch) is brought to its final weight by adding the remaining water. This compounding is carried out in a manner so that a significant viscosity increase is avoided. The viscosity of the bulk product thus preferably remains below 5 mPas, preferably below 3.2 mPas during the compounding step (viscosity determined after filtration upon dissolution in an amount of 20 mg in 1 ml of 2.5% (w/V) aqueous mannitol solution). This can be achieved by wetting the peptide at a high stirring speed for a relatively short time period (up to 30 minutes) and then dissolving the peptide at a reduced stirring speed to avoid foaming and aggregation (generally for 30 to 90 minutes). The temperature is usually kept within a range of 6-15° C. The stirrer is preferably one that provides turbulent mixing without vortex.

Filtration

The bulk drug product is then preferably sterile filtered, e.g. through two sterilizing grade filters placed in series, by pressurizing the formulated bulk with nitrogen.

Filling

Sterilized vials are filled with the filtered bulk drug product and semi-stoppered (freeze-drying position) under aseptic conditions.

Freeze-Drying

The freeze-dryer is preferably steam sterilized before use. The vials are the placed on the freeze-dryer shelves. The subsequent freeze-drying process preferably comprises the steps of freezing, main drying (sublimation), and secondary drying. Preferred conditions are as follows:

The freeze-drying process preferably comprises, or even consists of, three main steps, i.e. freezing, main drying (sublimation) and secondary drying.

Freezing

The vials are loaded onto refrigerated shelves maintained at 2 to 10° C., such as 5° C.

The shelves are cooled from e.g. 5° C. to −30 to −40° C., such as −35° C. The shelf temperature is maintained at e.g. −35° C. for minimum two hours to ensure complete freezing of the entire batch prior to commencement of primary drying.

Main Drying (Sublimation)

Main drying is performed by lowering the chamber pressure (preferably to 0.100 mBar or less) and increasing the shelf temperature (preferably to 10 to 20° C., such as +17° C.).

The main drying time proceeds for at least 15 hours.

Secondary Drying

After completion of the primary dying process, chamber pressure is reduced (preferably to 0.01 mBar or less) and the shelf temperature is increased (preferably to 20 to 30° C., such as 25° C.). Secondary drying is typically completed within 7 hours.

The lyophilized drug product is then labeled and packaged and combined with the appropriate amount of reconstitution liquid.

The reconstitution liquid is selected depending on the viscosity of the drug substance. If drug substance (1) is used as starting material for production process A, i.e. a lyophilized drug substance that shows a viscosity of less than 3.2 mPas, preferably between 1.15 and 2 mPas (upon dissolution in an amount of 20 mg in 1 ml of 2.5 (w/v) % aqueous mannitol solution), the resulting lyophilized drug product is preferably combined with water for injection (WFI) as reconstitution liquid. If the lyophilized drug product is reconstituted with WFI, the viscosity is generally in the range of 2 to 15 mPas (as measured upon dissolution of 20 mg degarelix (free base) in 1 ml WFI). A drug product with a viscosity within this range was found to provide a sufficient depot release of degarelix in vivo.

Production Process B of the Degarelix Drug Product

Production process B is a method for producing degarelix drug product comprising a lyophilized degarelix drug product and a liquid for reconstitution (reconstitution fluid) which, upon reconstitution with said liquid in an amount of 20 mg degarelix free base/ml, shows a viscosity of up to 15 mPas, preferably within a range of 2 to 12 mPas, comprising the steps of:

a. Dissolving a lyophilized degarelix drug substance in a mannitol containing aqueous solution to provide a degarelix-mannitol mixture;
   b. Lyophilizing the degarelix-mannitol mixture to provide the degarelix drug product, wherein a viscosity-reducing agent is added to the degarelix-mannitol mixture prior to lyophilization.

Step a may also be referred to as compounding step. In a preferred embodiment, filtration and vial filling are carried out after compounding and before freeze-drying so that the entire preferred production process B comprises the steps of:

Compounding to provide the unfiltered bulk drug product
   Filtration (sterile)
   Vial filling
   Freeze-drying/Lyophilization Production process B is identical to production process A, with the exception that in the compounding step, a viscosity-reducing agent, preferably a non-ionic surfactant is added prior to lyophilization. The non-ionic surfactant is preferably added in an amount of 0.0003 to 1.5 mg/ml to the bulk solution, corresponding to an amount of 0.001 to 5 mg/ml, more preferably 0.1 to 1 mg/ml, in the reconstituted drug product (e.g. when reconstituted to a degarelix concentration of 60 mg degarelix free base/ml). Preferred non-ionic surfactants are those with a linear alkyl chain having at least 8 carbon atoms (preferably without double bonds) and a carbohydrate moiety. Particularly preferred are those that are approved for subcutaneous injections, such as Tween 20 (Polysorbate 20). Other suitable non-ionic surfactants include Tocopheryl-polyethylene-glycol-1000-succinate (TPGS) and other Tweens.

As starting material for production process B, drug substance (2) is preferably used, i.e. a lyophilized drug substance that shows a viscosity of at least 3.2 mPas (upon dissolution in an amount of 20 mg degarelix free base in 1 ml of 2.5 wt. % aqueous mannitol solution). The resulting lyophilized drug product is typically combined with WFI as reconstitution liquid. If the lyophilized drug product is reconstituted with WFI, the viscosity is generally in the range of 2 to 15 mPas (as measured upon dissolution of 20 mg degarelix free base in 1 ml WFI). A drug product with a viscosity within this range was found to provide a sufficient depot formation for delayed release of degarelix in vivo.

Production process B is particularly preferred for degarelix products that have a relatively high degarelix concentration upon reconstitution, such as 50 mg degarelix free base/ml or more, e.g. 60 mg degarelix free base/ml (240 mg drug product).

Novel Degarelix Drug Product

Production process B provides a novel degarelix drug product that differs from known drug products in that the reconstituted drug product contains a viscosity-reducing agent. The viscosity-reducing agent is the one used in step B, preferably a non-ionic surfactant.

The present invention thus provides a degarelix drug product which comprising a lyophilized degarelix drug product and a liquid for reconstitution which, upon reconstitution with said liquid in an amount of 20 mg degarelix free base/ml, shows a viscosity of up to 15 mPas, preferably within a range of 2 to 12 mPas, and contains a viscosity-reducing agent in an amount of 0.001 to 5 mg/ml, more preferably 0.1 to 1 mg/ml.

EXPERIMENTAL SECTION

Example 1: Purification, Deaggregation and Lyophilisation

Crude Degarelix was synthesized as described in WO2012/055905 A1, up to Step 12 in Example 5. Step 13 as disclosed in WO2012/055905 A1 was replaced by the following steps, In summary, the purification process of crude degarelix drug substance, obtained after the last deprotection step, consists of three preparative reversed phase chromatography (RPC) steps, where the third RPC step primarily is a desalting step.

Step 13 (Purification Step):

Crude degarelix solution from step 12 in WO02012/055905A1 was applied to a column packed with reversed phase material, pre-equilibrated with buffer (90% of 0.12% TFA and 10% of EtOH). Load: ≤30 g/L column volume. The column was washed and eluted with a gradient: Buffer (EtOH 29% to 50 and 0.12% TFA (aq) 71% to 50%). The fractions obtained were analysed, and combined in such a way that the purity of the main pool fulfilled the acceptance criterion for the process control.

When elution was checked by HPLC method, purity is ≥95%.

Step 14 (Purification Step):

The main pool obtained in the step 13 was diluted twice with water and applied to the column packed with reversed phase material, pre-equilibrated with buffer (90% of 1% AcOH and 10% of EtOH). Load: ≤25 g/L column volume. The column was first washed with a first buffer (10% of EtOH and 90% of 0.5 mol/L AcONH4) and then with a second buffer (90% of 1% AcOH and 10% of EtOH).

The column was then eluted with a mixture of buffer and ethanol (76% of 1% AcOH and 24% of EtOH). The fractions obtained were analyzed, and combined in such a way that the purity in the main pool fulfilled the acceptance criteria for the process control.

When elution was checked by "HPLC method", purity is ≥97.5%.

Step 15 (Pre-Concentration/Salt Exchange):

The main pool obtained in the step 14 was diluted twice with water and applied to the column packed with reversed phase material, pre-equilibrated with buffer (90% of 1% AcOH and 10% of EtOH). Load: ≤18 g/L column volume. The column was first washed with a first buffer (10% of EtOH and 90% of 0.5 mol/L AcONH4) and then with a second buffer (90% of 1% AcOH and 10% of EtOH). The column was then eluted with a mixture of buffer and ethanol (50% of 1% AcOH and 50% of EtOH).

As an alternative, degarelix can be eluted with a solution of AcOH/MeCN/water, such as 12% AcOH and 22% MeCN in water.

Step 16 (Concentration-De-Aggregation-Lyophilization):

Prior to lyophilisation, the pool of pure degarelix solutions from step 15 was concentrated below 40° C. Aqueous acetic acid and water were added to the concentrated solution, to give a concentration below 15 g/L, and an acetic acid concentration of 30%. This solution was then filtered and lyophilised to yield degarelix drug substance.

Pressure: ≤0.5 mbar during the primary and secondary drying

Temperatures: End freezing temperature: ≤−30° C.
   End primary drying temperature: 20° C.
   End secondary drying temperature: 20° C.

Time: 5 days

Results

The viscosity of the drug substance obtained by the sequence of steps was below 2.5 mPas, as determined in a concentration of 20 mg/ml in 2.5 (w/V) % mannitol solution.

Example 2: Method for Measuring Viscosity for Drug Substance and Drug Product

Determination of the viscosity of the drug substance and drug product solution is based on the current edition of Ph. Eur. and USP procedure using a rotating viscometer equipped with a cone-plate measuring system with D=60 mm and 1°. The shear rate is increased from 0 to 500 $s^{-1}$ in 20 steps, using a controlled rate (CR) rotation step program at a constant temperature of 20±0.2° C., making certain that the system reaches equilibrium before the viscosity is recorded at a shear rate of 500 $s^{-1}$.

Example 3: Method for Measuring Optical Density for Drug Substance and Drug Product Equipment and Materials
   UV spectrophotometer
   UV light transmitting cuvettes, 10 mm path.
   Cuvette lids
   Water for Injection (used for reconstitution of degarelix drug product and in the reference cell)

Performance of Analysis

Between reconstitution and measurement the reconstituted samples must be kept at 22° C.±1° C.

The drug substance vial is reconstituted 2.5% aqueous mannitol solution in water (w/V). The drug product vial is reconstituted with water for injection. Dispense the solvent into the vial and swirl the vial until reconstitution is complete or use a vortex for a few seconds. The liquid should look clear and no undissolved powder or particles are visible. Keep the vial upright and do not shake. The sample is measured at 350 nm, 120 minutes after addition of the solvent.

Four minutes before the measurement, the sample has to be homogenized by gently turning the cuvette five times back and forth through approximately 180 degrees. The four minute delay allows any air bubbles to disperse before the reading.

The absorption caused by the cuvette and by the water for injection has to be deducted from the read-off of the sample.

Example 4: Spray Drying

Preparation of Feed

In the preparation of the feed, the weighed amount of degarelix, shown in the table below, was dissolved using a magnetic stirrer. The different feed solutions, W—VI and AI-IV were prepared by addition of Milli-Q water, or pure glacial acetic acid (99.9%) in the following manner:

a. Batch W-IV: the appropriate volume of water was added to the weighed amount of degarelix
b. Batch A-I to A-Ill: for each experiment, acetic acid solutions were prepared by diluting 99.0% glacial acetic acid with Milli-Q water resulting in 30, 5, 2 percent solutions, to which the weighed amount of degarelix as added Prior to all of the spray-drying runs, the reconstituted peptide was filtered into a measuring flask through a 0.20 μm Sartoriuos Ministar filter prior to spray-drying.

Spray-Drying

Prior to spray-drying, the inlet temperature and the feed rate were adjusted. The tubing of the pump was placed in the feed solution, and the drying was initiated. When the drying was completed, the inlet temperature was allowed to drop to 700° C. before the cyclone and the collection vessel were dismantled for powder collection. The powder was collected with brushes into Petri dishes, which were weighed before and after collection to determine the yield.

Overview of the Setting Applied for Spray-Drying

| Parameters | W-IV | A-I | A-II | A-III |
|---|---|---|---|---|
| Inlet temperature, ° C. | 120 | 120 | 120 | 120 |
| Outlet temperature, ° C. | 85 | 85 | 85 | 85 |
| Atomising air flow, L/h | 600 | 600 | 600 | 600 |
| Liquid feed rate, mL/min. | 3 | 3 | 3 | 3 |
| Aspirator rate, m3/h | 30 | 30 | 30 | 30 |
| Solvent | water | Aq. 30% AcOH | Aq. 5% AcOH | Aq. 2% AcOH |
| Solution volume, mL | 25 | 25 | 25 | 25 |
| Amount of degarelix | 1 | 1 | 1 | 1 |
| Concentration of feed, % | 4 | 4 | 4 | 4 |

The viscosity of reconstituted degarelix spray-dried from acetic acid solutions of four different concentrations (A-I to A-Ill) compared to one batch of degarelix spray-dried from water (W-IV)

|            | Batch no. |      |      |       |
|------------|-----------|------|------|-------|
|            | W-IV      | A-I  | A-II | A-III |
| Viscosity, mPas * S | 2.40 | 1.68 | 2.11 | 2.10 |

Example 5: Column Concentration—Lyophilization

The pool from step 14 of Example 1 was diluted with water and applied to a column packed with reversed phase material. After rinsing the column with 1% AcOH in water degarelix was eluted with 35% AcOH in water. Fractions were adjusted to contain 35 g degarelix/l, 27% AcOH (Sample 1) and 15 g degarelix/l, 30% AcOH (Sample 2). The adjusted fractions were freeze-dried and analysed. Results: see Table below:

| Analysis on drug substance | Sample 1 | Sample 2 |
|---|---|---|
| Water (w/w) | 2.1% | 2.5% |
| Residual AcOH (w/w) | 7.2% | 7.0% |
| OD 20 mg/ml (15 min/6 h) | <0.02 AU/0.02 AU | <0.02 AU/0.02 AU |
| Viscosity 20 mg/ml | 1.88 mPas | 1.94 mPas |

Example 6: Manufacture of Degarelix Drug Substance and Deaggregation Studies

Materials
De-aggregation studies of purified, crude drug substance
Crude, purified degarelix was supplied at a concentration of 57.4 mg/ml
Acetic acid 100% was supplied by Merck
De-aggregation equipment:
  Compounding vessel: 300 ml double walled glass vessel
  Blue Cap bottles, 50 or 100 ml
  Magnet
  Magnetic stirrer
Primary packaging:
  Colourless 20R glass vials. Vials were washed and dried in a heat chamber.
  20 mm freeze-drying stoppers type I according to Ph. Eur/USP 20 mm Flip-Off Caps
Manufacturing of Drug Products Using the De-Aggregated Drug Substances
  Two experimental drug substances were used. As a control, a commercial drug substance is used.
  Mannitol: D (−) mannitol (PF-05-0232)
  Primary packaging:
    Colourless 10R glass vials (according to DIN ISO 8362). Vials are washed and dried in a heat chamber.
    20 mm freeze-drying stoppers type I according to Ph. Eur/USP (type 1319, rubber W4416/50/grey, The West Company)
    20 mm Flip-Off Caps (The West Company)
Methods
De-Aggregation Experiments Using a Drug Substance Stock Solution
Temperature During the Experiments:
  During the de-aggregation studies the temperature was set to 5, 20, 25, or 35° C.
Concentration of Degarelix Drug Substance in Stock Solutions During the Experiments:
  The concentration of degarelix drug substance was 5, 15, 25, or 35 mg/ml.
Concentration of Acetic Acid During the Experiments:
  The concentration of acetic acid is 13, 15, 18, 20, 22, 26, 30, 35 or 40%.
Analysis Performed During the Experiments:
  Viscosity: Take out ~1.2 ml at T=1, 60, 120, and 240 min. If it fits better into the schedule to take the sample at another time point, then this can be done provided the correct time is written into the formulation record. However, the sampling point at T=1 min should be kept.
  Optical Density (OD): A sample (~1 ml) should be taken at the end of each experiment for measurement of the final optical density.
De-aggregation Experiment Protocol, total volume 20 or 69 ml:
  1. Weigh the required amount of stock solution into a beaker. Equilibrate to the desired temperature
  2. Weigh the required amount of acetic acid (100%) into a beaker
  3. Mix the acetic acid (100%) with 3 or 10 ml of milli-Q water and equilibrate to the desired temperature
  4. Mix the degarelix stock solution with the acetic acid/milli-Q water solution
  5. Fill milli-Q water up to 20 or 69 ml
  6. Mix thoroughly
  7. Take samples for viscosity and optical density as described above. Note the appearance of the solution during the experiment
Settings for De-Aggregation of the Two 69 ml Degarelix Stock Solution:
Degarelix drug substance conc. 25 mg/ml in both experiments
Acetic acid: 10% or 13%
Temperature: 5° C.
  Filling the two test de-aggregated drug substances (69 ml) into vials and freeze-drying: The de-aggregated solutions were filled immediately into 20R vials. 5 ml were filled into each vial. The vials and bulk should be kept cold during filling (preferably between 5-10° C.). As soon as the vials were filled they were placed in the freeze dried and the program was initiated.
  Subsequent to freeze drying and closing of the vials, the vials were stored in the freeze dryer at 5° C. until de-loading.
  The two freeze dried drug substances were subjected to the following analyses:
Viscosity was measured on samples of 20 mg/ml free base
Optical density is measured on samples of 20 mg/ml
Content of degarelix
Content of acetate
  Results

| Temp. (° C.) | Degarelix conc. mg/ml | AcOH conc. (%) | Viscosity @ 500 mPa * s Time = 240 min | Optical Density Time = 240 min |
|---|---|---|---|---|
| 5  | 5  | 40 | 1.9 | 0.00 |
| 5  | 25 | 13 | 2.3 | 0.10 |
| 5  | 25 | 15 | 1.9 | 0.09 |
| 5  | 25 | 20 | 1.7 | 0.06 |
| 5  | 35 | 26 | 1.9 | 0.08 |
| 20 | 15 | 30 | 1.8 | 0.03 |
| 25 | 25 | 20 | 2.0 | 0.10 |
| 35 | 25 | 15 | 7.2 | 0.86 |
| 35 | 25 | 18 | 2.1 | 0.07 |
| 35 | 25 | 20 | 1.7 | 0.05 |
| 35 | 35 | 22 | 2.1 | 0.13 |
| 35 | 35 | 26 | 1.9 | 0.10 |

-continued

| Temp. (° C.) | Degarelix conc. mg/ml | AcOH conc. (%) | Viscosity @ 500 mPa * s Time = 240 min | Optical Density Time = 240 min |
|---|---|---|---|---|
| 35 | 35 | 30 | 2.0 | 0.07 |
| 35 | 35 | 35 | 2.1 | 0.08 |

Example 7: Production of Drug Product without Viscosity-Reducing Agent

Compounding of Lab-Scale Drug Product Batches Using the Two De-Aggregated Drug Substances The excipients listed below in Table 1 are used in all compounding experiments.

| Excipients |
|---|
| Mannitol |
| Milli-Q water |

Compounding Equipment:
Compounding vessel: 300 ml double walled glass vessel
Blue Cap bottles, 100 ml
Magnet
Magnetic stirrer
Primary Packaging:
  Colourless 10R glass vials. Vials were washed and dried in a heat chamber.
  20 mm freeze-drying stoppers type I
  20 mm Flip-Off Caps
Study Description
  Degarelix bulk solutions containing 20 mg/g degarelix and 25 mg/g mannitol are compounded using different batches of drug substance and different settings of temperature.
  The viscosities of the bulk solutions is measured during/after compounding on two occasions (after dissolution and at t=120 minutes).
Bulk Composition:
  The batch size and composition of the two bulk solutions is presented in Table 2.

TABLE 1

| Batch size and composition of the bulk solutions | |
|---|---|
| Batch size (g) | 50 |
| Drug substance (g) | 1.000 g/degarelix free base content drug substance |
| Mannitol (g) | 1.25 |
| Milli-Q water - Total (g) | Ad. 50 |

Experimental Design:
The compounding parameters are given below in Table 2.

TABLE 2

| Compounding parameters | |
|---|---|
| Time | Parameters |
| Drug substance | Test drug substance batches |
| Temperature | 15° C. |
| Stirring speed | 50 rpm |
| Water, starting volume | 80% |

Compounding:
The compounding is performed with the stirrer positioned at the centre. Before commencing the experiments the centre position should be fixed.
1. Weigh the required ingredients
   40 g of Milli-Q water into the compounding vessel.
   1.25 g of mannitol into a suitable container.
   Weigh exact amount of degarelix drug substance (see Table 2) into a suitable container.
   Weigh the remaining amount of Milli-Q water into a suitable container.
2. Connect the double walled compounding vessel containing the Milli-Q water to the cooling circulator. Connect a second double walled vessel in series. The container containing the rest water is placed in the second double walled vessel in order that it will equilibrate to the correct temperature before being added to the bulk (step 9).
3. Carefully place the stirring magnet in the compounding vessel. Set the stirring rate to 50 rpm using the tachometer.
4. Set the cooler to the correct temperature, start the stirring and add the mannitol to the compounding vessel. Stir until mannitol has dissolved.
5. Allow the system to equilibrate to the set temperature.
6. Measure the temperature in the mannitol solution.
7. Remove the stirrer. Start the timer and immediately add the drug substance. Then reinsert the stirrer.
8. At t=5 minutes add the rest of the Milli-Q water, evenly over the surface of the drug substance using a glass Pasteur pipette.
9. When only a few lumps are left, rinse down drug substance from the sides of the vessel with the dissolution medium.
10. When the drug substance is completely dissolved make a note of the time and measure the temperature. Take out a sample for viscosity measurement of the bulk.
11. Continue the experiment until t=120 minutes. Take out a sample for viscosity measurement of the bulk.
Filtering
The bulks will not be filtered because it is expected that at least one of the batches will be highly aggregated and therefore very difficult to filter. Also, the batches will not be used for purposes where sterility is required.
Filling
Fill 6.40 g bulk into 10R vials. The vials and bulk should be kept cold during filling (preferably between 5-10° C.). As soon as the vials are filled they should be placed in the freeze dried and the program should be initiated. Each bulk should result in approx. 6-7 vials.
Results
18 different drug substance batches, with different viscosities as indicated in the table below, were processed as described above. The viscosity of the corresponding drug products was determined as follows:

| Batch | Viscosity DS (20 mg/ml) mPas | Viscosity DP (20 mg/ml) mPas |
|---|---|---|
| 1 | 2.3 | 5.8 |
| 2 | 2.3 | 7.81 |
| 3 | 2.1 | 4.75 |
| 4 | 2.3 | 8.62 |
| 5 | 2.1 | 7.85 |
| 6 | 2.1 | 7.09 |

-continued

| Batch | Viscosity DS (20 mg/ml) mPas | Viscosity DP (20 mg/ml) mPas |
|---|---|---|
| 7 | 2.3 | 7.76 |
| 8 | 2.1 | 7.69 |
| 9 | 2.1 | 7.96 |
| 10 | 2.3 | 8.1 |
| 11 | 1.8 | 7.82 |
| 12 | 1.7 | 4.14 |
| 13 | 2.3 | 8.46 |
| 14 | 2.3 | 9.57 |
| 15 | 2.3 | 10.96 |
| 16 | 2.3 | 8.47 |
| 17 | 2.5 | 8.05 |
| 18 | 2.5 | 10.4 |

These results are graphically illustrated in FIG. 1. FIG. 1 shows a correlation between drug substance viscosity and drug product viscosity.

Example 8: Production of Drug Product with Viscosity-Reducing Agent

Experiment 1: Surfactants Tested (Reconstitution Using WFI/Surfactant Solution)

Procedure:
Degarelix batch reconstituted using WFI (as control) and using WFI containing the surfactants. The vials are reconstituted to 60 mg/ml degarelix. The drug product batch used for these experiments had a bulk viscosity of approx. 3.8 mPas.
TPGS and Tween 20 were prepared in solutions containing 1 mg/ml (0.1% solutions)
OD (absorbance) was measured at 350 nm
Absorbance was registered after 30 min, 60 min, 120 min and 24 hours Result:
Both TPCG and Tween 20 reduced the optical density to a level below the control.

Experiment 2: Reconstitution of Degarelix Vials with [WFI+Tween 20] does not Alter the In-Vitro Release Profile (IVD Assay) at 40 mg/ml of Degarelix Tween 20 concentrations tested:
1 mg/ml; 0.5 mg/ml; 0.25 mg/ml;
Control: WFI
Results: The in-vitro release profiles are not altered by the addition of Tween-20.

Example 9: Drug Product Viscosity and Bioavailability

Summary
A multivariate data analysis was undertaken with a set of data from n=38 batches of degarelix drug products, including in vivo pharmacokinetic data (rat model).
A relationship between physico-chemical characteristics and in vivo pharmacokinetics in a rat model was established. The study revealed that the viscosity of the reconstituted degarelix product appears to be the prominent and only parameter with some ability to predict in vivo performance of the depot.

Introduction
Degarelix drug product is manufactured as a freeze-dried product containing mannitol. The products are used as investigational medicinal products in clinical studies. Several formulations were produced, containing various amounts of degarelix per vial, namely 10 mg, 20 mg, 40 mg, 88 mg, 128 mg, 120 mg (40 mg/ml), 180 mg (60 mg/ml) and 240 mg (60 mg/ml) and different ratios of degarelix/mannitol.

Materials
Approximately 40 different batches of degarelix have been produced with different batches of degarelix substance and formulations. The standard degarelix concentration in the bulk is 20 g/l unless otherwise stated.

Methods
Physico-Chemical Methods
The different methods to characterise aggregation were selected from multivariate data analysis. Data from n=38 batches were compiled. However, smaller populations were used for some methods that were only implemented with some formulations (e.g. measurements at 40 mg/ml not performed with the 20 mg formulation).

Rat Bioassay
A standardised rat assay consisting in following the pharmacokinetic profile of degarelix over 28 days was used. In order to avoid local side effects, the rats were given degarelix as a 20 mg/ml suspension with an injection volume of 100 μl. Groups of n=8 rats were used, all treated with the reconstituted suspension originating from one single vial. Plasma concentrations were initially measured at 2 hrs, 1 day, 7 day and 28 day and partial AUC calculated as AUC 0-7 days and AUC 7-28 days. The design was then changed with measurement of plasma concentration (Cp)-2 hrs being skipped and being replaced by Cp-3 days. Likewise, AUC 0-7 days was replaced by AUC 1-7 days. This explains the discontinuities in the population sizes of some of the in vivo variables.

Multivariate Data Analysis
Given the size of the data set, an approach by multivariate data analysis (PCA and PLS) with the Simca-P, version 10 software (Umetrics AB, SE-Umeå) was implemented. Data were handled as previously, including soft block scaling (¼ root), scaling to unit variance (UV) and centering. Turbidity data were log transformed to improve data distribution. In vivo Cp data were also log transformed to stabilise the variance.

Relationship Between Drug Product Physico-Chemistry and In Vivo Performance in a Rat Model
Relationship Between Physico-Chemistry and In Vivo Performance
A first model was calculated based on 2 components. The goodness of fit (R2=0.58) was relatively low given the high variability of the biological data (20-30%), but the goodness of predictability (Q2=0.35) was satisfactory (R2-Q2 should be in the range of 0.2 to 0.3). It could be seen from the loading scatter plot (not shown) that variables such as turbidity measured at 20 mg/ml and acetate content were not influential.

A new model was therefore generated excluding these 3 variables (2 turbidity variables measured at 20 mg/ml and acetate), based on 2 significant components and yielding to similar data description (R2=0.53) but improved predictability (Q2=0.42). Best explained and predicted rat variables were plasma concentrations at 3 days and 28 days (Cp-3d, Cp-28d), and the area under the curve between day 1 and day 7 (AUC 1-7d).

The coefficient overview plot indicated that larger influences were carried by the viscosity data respectively at 20 mg/ml and then at 40 mg/ml, all significant at a confidence level of 0.95 for every biological variable. Specific surface area and turbidity were clearly of lesser influence and were not significant, even at a confidence level of 0.90.

The relationship between dynamic viscosity measured at 20 mg/ml and best fitted biological variables is shown in FIGS. 2 and 3.

CONCLUSION

A solid relationship (R2=0.53) was established between viscosity of the constituted product and in vivo performance as investigated in a rat model. In both cases, a higher viscosity yielded to a reduced release from the depot. Other physico-chemical variables were not relevant with the exception of acetate content for in vitro dissolution. Therefore, the viscosity of constituted degarelix product appears to be the prominent parameter with some ability to predict in vitro release and in vivo performance of the depot.

The invention claimed is:

1. A lyophilized degarelix drug substance having a viscosity of up to 3.2 mPas, as determined upon dissolution in an amount of 20 mg degarelix free base in 1 ml of water containing 2.5% (w/V) mannitol, and the lyophilized degarelix drug substance has an acetic acid concentration ranging from 4.5% to 10.00% (w/w) and a water content of 10% (w/w) or less, wherein the lyophilized degarelix drug substance is prepared by a method, comprising:
   a. purifying degarelix obtained by a liquid or solid phase peptide synthesis to obtain a degarelix solution with a purity of at least 95%, as determined by high-performance liquid chromatography (HPLC);
   b. evaporating a solvent to concentrate the degarelix solution to obtain aggregated degarelix;
   c. deaggregating the aggregated degarelix with acetic acid to obtain deaggregated degarelix; and
   d. lyophilizing the deaggregated degarelix to provide the lyophilized degarelix drug substance.

2. The substance according to claim 1, wherein the purity of the degarelix solution obtained in step (a) is at least 97.5%, as determined by HPLC.

3. The substance according to claim 1, wherein step (a) further comprises a pre-concentration step comprising pre-equilibrating a pre-concentration column with a pre-equilibrating buffer; diluting the degarelix with water; loading the degarelix onto the pre-concentration column; washing the pre-concentration column with a first washing buffer comprising ethanol and aqueous ammonium acetate, and then a second washing solution comprising ethanol, acetic acid, and water; and eluting degarelix from the pre-concentration column.

4. The substance according to claim 1, wherein the evaporating of step (b) is carried out at or below 40° C.

5. The substance according to claim 1, wherein the deaggreagated degarelix obtained in step (c) has an acetic acid concentration ranging from 6% to 40% (v/v).

6. The substance according to claim 1, wherein step (c) is carried out over 1 to 15 hours.

7. The substance according to claim 1, wherein step (d) comprises a primary drying procedure and a secondary drying procedure, both of which are conducted at a pressure less than or equal to 0.5 mbar.

8. The substance according to claim 7, wherein the primary drying procedure is carried out at a primary drying temperature of about 20° C.

9. The substance according to claim 7, wherein the secondary drying procedure is carried out at a secondary drying temperature ranging from 15° C. to 25° C.

10. The substance according to claim 1, wherein step (d) is carried out over a period of about 5 days.

11. A method of preparing a lyophilized degarelix drug substance, comprising:
    a. purifying degarelix as obtained by liquid or solid phase peptide synthesis to obtain a degarelix solution with a purity of at least 95%, as determined by high-performance liquid chromatography (HPLC);
    b. isolating the degarelix solution via lyophilization to obtain isolated degarelix;
    c. dissolving the isolated degarelix to obtain a reconstituted degarelix solution, wherein the reconstituted degarelix solution of step (c) has a degarelix concentration ranging from 10 to 20 g degarelix/L of aqueous 2% acetic acid; and
    d. lyophilizing the reconstituted degarelix solution to provide the lyophilized degarelix drug substance,
    wherein the lyophilized degarelix drug substance has a viscosity of less than 3.2 mPas, as determined upon dissolution in 1 mL of aqueous 2.5% (w/V) mannitol solution of an amount of the lyophilized degarelix drug substance necessary to achieve a degarelix concentration of 20 mg/mL; and wherein the lyophilized degarelix drug substance has an acetic acid concentration ranging from 4.5% to 10.00% (w/w) and a water content of 10% (w/w) or less.

12. The method according to claim 11, wherein the purity of the degarelix solution obtained in step (a) is at least 97.5%, as determined by HPLC.

13. A method of preparing a degarelix drug substance, comprising the following steps a, b, and d; or a, c, and d:
    a. purifying degarelix as obtained by liquid or solid phase peptide synthesis to obtain a degarelix solution with a purity of at least 95%, as determined by high-performance liquid chromatography (HPLC); and
    b. evaporating a solvent to concentrate the degarelix solution to obtain aggregated degarelix and deaggregating the aggregated degarelix with acetic acid;
    c. loading the degarelix solution onto a chromatographic column and eluting degarelix from the column with acetic acid;
    d. isolating the degarelix via spray drying to provide the degarelix drug substance, and
    wherein the degarelix drug substance has a viscosity of less than 3.2 mPas, as determined upon dissolution in 1 mL of aqueous 2.5% (w/V) mannitol solution of an amount of the degarelix drug substance necessary to achieve a degarelix concentration of 20 mg/mL; and wherein the degarelix drug substance has an acetic acid concentration ranging from 4.5% to 10.00% (w/w) and a water content of 10% (w/w) or less.

14. The method according to claim 13, wherein the purity of the degarelix solution obtained in step (a) is at least 97.5%, as determined by HPLC.

15. The method according to claim 13, wherein the spray drying of step (d) comprises an inlet temperature of about 120° C., an outlet temperature of about 85° C., an atomizing air flow rate of about 600 L/h, a liquid feed rate of about 3 mL/min, and an aspirator rate of about 30 m$^3$/h.

16. A method of preparing a degarelix drug substance, comprising:
    a. purifying degarelix as obtained by liquid or solid phase peptide synthesis to obtain a degarelix solution with a purity of at least 95%, as determined by high-performance liquid chromatography (HPLC); and
    b. isolating the degarelix via spray drying to provide the degarelix drug substance, wherein the degarelix drug substance provided has a viscosity of less than 3.2 mPas, as determined upon dissolution in 1 mL of aqueous 2.5% (w/V) mannitol solution of an amount of the degarelix drug substance necessary to achieve a degarelix concentration of 20 mg/mL; and wherein said degarelix drug substance has an acetic acid concentration ranging from 4.5% to 10.00% (w/w) and a water content of 10% (w/w) or less.

17. A lyophilized degarelix drug substance prepared by the method according to claim 11.

18. A lyophilized degarelix drug substance prepared by the method according to claim 13.

19. A lyophilized degarelix drug substance prepared by the method according to claim 16.

* * * * *